(12) United States Patent
Ulijn et al.

(10) Patent No.: US 11,021,516 B2
(45) Date of Patent: Jun. 1, 2021

(54) SELF-ASSEMBLING PEPTIDE POLYMER

(71) Applicants: Research Foundation of the City University of New York, New York, NY (US); University of Strathclyde, Glasgow (GB); Carnegie Mellon University, Pittsburgh, PA (US)

(72) Inventors: Rein V. Ulijn, New York, NY (US); Ayala Lampel, Bronx, NY (US); Tell Tuttle, Glasgow (GB); Gary Scott, Glasgow (GB); Scott McPhee, New York, NY (US); Christopher Bettinger, Pittsburgh, PA (US)

(73) Assignees: Research Foundation of the City University of New York, New York, NY (US); University of Strathclyde, Glasgow (GB); Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 16/332,231

(22) PCT Filed: Sep. 11, 2017

(86) PCT No.: PCT/US2017/050953
§ 371 (c)(1),
(2) Date: Mar. 11, 2019

(87) PCT Pub. No.: WO2018/093449
PCT Pub. Date: May 24, 2018

(65) Prior Publication Data
US 2019/0233473 A1     Aug. 1, 2019

Related U.S. Application Data

(60) Provisional application No. 62/385,544, filed on Sep. 9, 2016.

(51) Int. Cl.
   *C07K 5/087*     (2006.01)
   *C08G 69/10*     (2006.01)
   (Continued)

(52) U.S. Cl.
   CPC ............ *C07K 5/0812* (2013.01); *B82Y 40/00* (2013.01); *C07K 5/0819* (2013.01); *C08G 69/10* (2013.01); *A61K 38/00* (2013.01)

(58) Field of Classification Search
CPC ...... A61K 38/00; B82Y 40/00; C07K 5/0812; C07K 5/0815; C07K 5/0819; C08G 69/10
See application file for complete search history.

(56) References Cited

U.S. PATENT DOCUMENTS

| 4,908,404 A | 3/1990 | Benedict et al. |
| 8,722,377 B2 | 5/2014 | Konishi et al. |

(Continued)

FOREIGN PATENT DOCUMENTS

| WO | WO2014080376 | 5/2014 |
| WO | WO2015177569 | 11/2015 |
| WO | WO2016055810 | 4/2016 |

OTHER PUBLICATIONS

Liu et al., Release of free amino acids upon oxidation of peptides and proteins by hydroxyl radicals, Anal Bioanal. Chem., vol. 409: 2411-2420 (Jan. 2017) (Year: 2017).*

(Continued)

*Primary Examiner* — Randall L Beane
(74) *Attorney, Agent, or Firm* — Peter J. Mikesell; Schmeiser, Olsen & Watts, LLP

(57) ABSTRACT

A self-assembling peptide is provided that is enzymatically oxidized to form a polymeric pigment. The monomeric peptide has three amino acids (tyrosine (Y), one phenylalanine (F), and one aspartic acid (D) or one lysine (K)) and, following self-assembly and treatment with a tyrosinase (Continued)

5 Claims, 15 Drawing Sheets

(51) Int. Cl.
*B82Y 40/00* (2011.01)
*C07K 5/093* (2006.01)
*A61K 38/00* (2006.01)

(56) References Cited

U.S. PATENT DOCUMENTS

| | | |
|---|---|---|
| 2005/0209145 A1 | 9/2005 | Stupp et al. |
| 2005/0272662 A1 | 12/2005 | Stupp et al. |
| 2011/0046414 A1 | 2/2011 | Zhang |
| 2013/0203149 A1 | 8/2013 | Konishi et al. |

OTHER PUBLICATIONS

Vij et al., Bioinspired Functionalized Melanin Nanovariants with a Range of Properties Provide Effective Color Matched Photoprotection in Skin, Biomacromolecules, vol. 17:2912-2919 and 35 pages of Supplemental Material (Jul. 31, 2016) (Year: 2016).*
Gao et al., Dual enzymes regulate the molecular self-assembly of tetra-peptide derivatives, Soft Matter, vol. 7:10443-10448 (2011) (Year: 2011).*
Frederix et al., Exploring the sequence space for (tri-)peptide self-assembly to design and discover new hydrogels, Nature Chemistry, vol. 7:30-37 (Jan. 2015) (Year: 2015).*
Hsiao et al., Serendipitous Discovery of Short Peptides from Natural Products as Tyrosinase Inhibitors, J. Chem. Inf. Model., vol. 54:3099-3111 and 11 pages of Supplemental (2014) (Year: 2014).*
Ryan et al., Effect of C-Terminal Modification on the Self-Assembly and Hydrogelation of Fluorinated Fmoc-Phe Derivatives, Langmuir, vol. 27:4029-4039 (Mar. 14, 2011) (Year: 2011).*
Pappas et al., Biocatalytic Pathway Selection in Transient Tripeptide Nanostructures, Angew. Chem. Int. Ed., vol. 54:8119-8123 and Supplemental pp. 1-11 (May 26, 2015) (Year: 2015).*
EPO; Extended European Search Report for corresponding European application 17871575.1; dated Apr. 8, 2020; 5 pages.
ISA/US; International Search Report/Written Opinion for International Application PCT/US17/50953; dated Apr. 26, 2018; 10 pages.
Lampel, A. et al.;Polymeric peptide pigments with sequence-encoded properties; Science; Jun. 9, 2017; pp. 1064-1068; vol. 356.
Botta, G. et al.; Selective Synthesis of DOPA and DOPA Peptides by Native and Immobilized Tyrosinase in Organic Solvent; ChemPLusChem; 2013; pp. 325-330; vol. 78.
Frederix, P. et al.; Exploring the sequence space for (tri)peptide self-assembly to design and discover new hydrogels; nature chemistry; Dec. 8, 2014; pp. 30-37; vol. 7.
Serpell, L.; Alzheimer's amyloid fibrils: structure and assembly; Biochimica et Biophysica Acta; 2000; pp. 16-30; vol. 1502.
Li, Y. et al.; Mass Spectrometric and Spectrophotometric Analyses Reveal an Alternative Structure and a New Formation Mechanism for Melanin; Analytical chemistry; Jul. 8, 2015; pp. 7958-7963; vol. 87.
Reches, M. et al.; Casting Metal Nanowires Within Discrete Self-Assembled Peptide Nanotubes; Science; Apr. 25, 2003; pp. 625-627; vol. 300.
Tuttle, T.; Computational approaches to understanding the self-assembly of peptide-based nanostructures; Israel Journal of Chemistry; Mar. 24, 2015.
Bellesia, G. et al.; Self-assembly of β-sheet forming peptides into chiral fibrillar aggregates; The Journal of Chemical Physics; Jun. 28, 2007; 12 pages; vol. 126.
Lee, O. et al.; Atomistic Molecular Dynamics Simulations of Peptide Amphiphile Self-Assembly into Cylindrical Nanofibers; J. Am. Chem. Soc.; Feb. 22, 2011; pp. 3677-3683; vol. 133.
Pappas, C. et al.; Biocatalytic Pathway Selection in Transient Tripeptide Nanostructures; Angewandte Chemie; May 26, 2015; pp. 1-6; vol. 54.

* cited by examiner

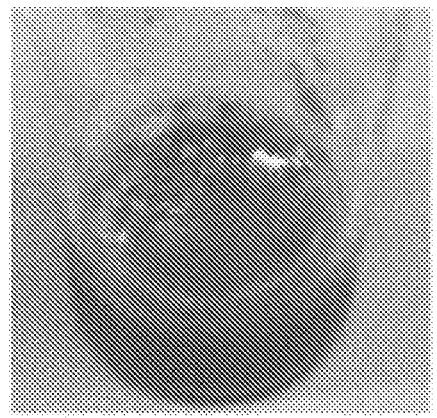 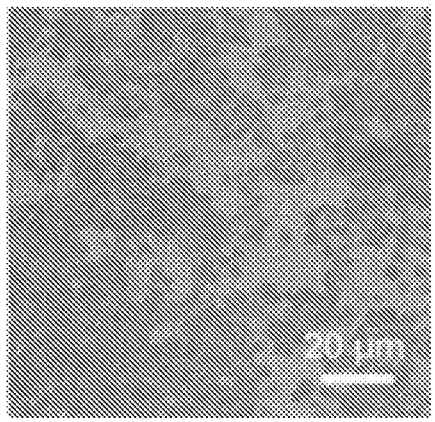
FIG. 5A    FIG. 5B
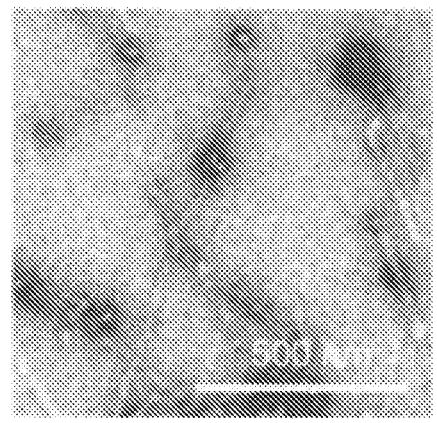 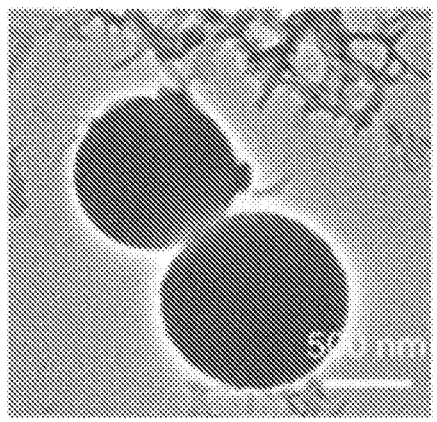
FIG. 5C
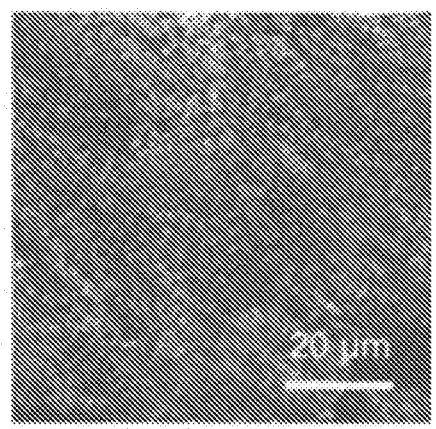
FIG. 5D

SELF-ASSEMBLING PEPTIDE POLYMER

CROSS-REFERENCE TO RELATED APPLICATIONS

This application claims priority to and is a non-provisional of U.S. Patent Application 62/385,544 (filed Sep. 9, 2016), the entirety of which is incorporated herein by reference.

STATEMENT OF FEDERALLY SPONSORED RESEARCH OR DEVELOPMENT

This invention was made with United States Government support under grant number FA9550-15-1-0192 awarded by the U.S. Air Force; grant numbers DMR-0820341 and DMR-1420073 awarded by the National Science Foundation; grant number CHE-1346572 awarded by the National Science Foundation and grant number DE-AC02-06CH11357 awarded by the U.S. Department of Energy. The government has certain rights in the invention.

BACKGROUND OF THE INVENTION

Melanins are a family of heterogeneous polymeric pigments that provide UV protection, structural support, coloration and free radical scavenging. Formed by oxidative oligomerization of catecholic small molecules, the physical properties of these materials are influenced by covalent and non-covalent disorder.

Melanin pigments are found in most life forms, from plants to bacteria to fungi and animals, where they have cardinal roles in organisms' coloration and protection from various (mainly photo- or free radical induced) cell damage-causing stresses. In addition to their protective roles, melanin pigments exhibit dynamic coloration and optoelectronic properties, inspiring efforts to design energy storage devices, environmental sensors surface-adherent coatings and colored films. The self-assembly and polymerization of natural melanin is regulated through complex pathways that include catalysis, templating, assembly, oxidation under confinement, in a process that is currently not fully understood. Laboratory-based strategies to synthesize melanin-based analogues are challenging to employ and difficult to control. Heterogeneous products typically consist of insoluble polymers with poorly defined chemical and structural composition, thereby limiting the technological utility of this class of materials.

The discussion above is merely provided for general background information and is not intended to be used as an aid in determining the scope of the claimed subject matter.

BRIEF DESCRIPTION OF THE INVENTION

A self-assembling peptide is provided that is enzymatically oxidized to form a polymeric pigment. The monomeric peptide has three amino acids (tyrosine (Y), one phenylalanine (F), and one aspartic acid (D) or one lysine (K)) and, following self-assembly and treatment with a tyrosinase enzyme oxidizes and polymerizes into a material with predetermined properties.

In a first embodiment, a polymeric peptide pigment is provided. The polymeric peptide pigment comprises a polymerized peptide that is the reaction product of oxidizing a plurality of peptides, wherein each peptide consists of three amino acids including one tyrosine (Y), one phenylalanine (F), and either one aspartic acid (D) or one lysine (K), wherein the tyrosine and the phenylalanine are adjacent one another.

In a second embodiment, a polymeric peptide pigment is provided. The polymeric peptide pigment is formed by a method comprising sequential steps of: forming an aqueous solution of a peptide consisting of three amino acids including one tyrosine (Y), one phenylalanine (F), and either one aspartic acid (D) or one lysine (K), wherein the tyrosine and the phenylalanine are adjacent one another; annealing by heating and subsequently cooling the aqueous solution to less than 30° C., the peptides self-assemble to form a supramolecular structure; and oxidizing the peptide to initiate a polymerization reaction, the polymerization reaction forming a polymeric peptide pigment.

In a third embodiment, a polymeric peptide pigment is provided. The polymeric peptide pigment is formed by a method comprising sequential steps of: forming an aqueous solution of a peptide consisting of three amino acids including one tyrosine (Y), one phenylalanine (F), and either one aspartic acid (D) or one lysine (K), wherein the tyrosine and the phenylalanine are adjacent one another; adjusting the aqueous solution to a pH of about 7.5, the peptides self-assemble to form a supramolecular structure; oxidizing the peptide to initiate a polymerization reaction, the polymerization reaction forming a polymeric peptide pigment.

In a fourth embodiment, a polymeric peptide pigment is provided. The polymeric peptide pigment is formed by a method comprising sequential steps of: forming an aqueous solution of a peptide consisting of three amino acids including one tyrosine (Y), one phenylalanine (F), and either one aspartic acid (D) or one lysine (K); annealing by heating and subsequently cooling the aqueous solution to less than 30° C., the peptides self-assemble to form a supramolecular structure; oxidizing the peptide to initiate a polymerization reaction, the polymerization reaction forming a polymeric peptide pigment.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 5A is a macroscopic image of the material formed following 24 h of enzymatic oxidation (0.2 µg/µL) of assembled KYF nanostructures (20 mM in water pH 7.5);

FIG. 5B depicts spherical structures formed by $KYF_{ox}$ polymeric pigment at the micron scale using optical microscopy;

FIG. 5C shows TEM micrographs of $KYF_{ox}$ polymeric pigment structures formed following 4 h and 24 h of oxidation;

FIG. 5D shows SEM micrographs of $KYF_{ox}$ spheres;

DETAILED DESCRIPTION OF THE INVENTION

Disclosed here in the use of tyrosine-containing tripeptides as tunable precursors for polymeric pigments. In these structures, phenols are presented in a (supra-) molecular context dictated by the peptide sequence by repositioning amino acids. Oxidative polymerization can be tuned in a sequence-dependent manner resulting in peptide sequence-encoded properties such as UV absorbance, morphology, coloration and electrochemical properties over a considerable range. Short peptides have low barriers to application and can be easily scaled, suggesting applications in cosmetics and biomedicine including cosmetic, personal care and food applications that provide coloration, pigmentation and/or ultraviolet (UV) protection. These could be formulated as a cream, gel or paste. Additional applications include ion storage for battery applications.

Without wishing to be bound to any particular theory, it is believed that supramolecular materials formed by peptide building blocks offer promise for the formation of synthetic melanin-like materials (or polymeric pigments) due to the ability to precisely control the presentation of chemical functionality and consequently reactivity, through non-covalent interactions. Even very short peptides, consisting of only two or three amino acids have been shown to self-assemble to form discrete nanoscale materials. Furthermore, combining supramolecular self-assembly with catalytic transformations provides spatiotemporal control over the assembly process, giving rise to materials with kinetically tunable properties. Thus, combining catalysis and self-assembly offers an attractive approach for aqueous materials processing.

Figure 1A:
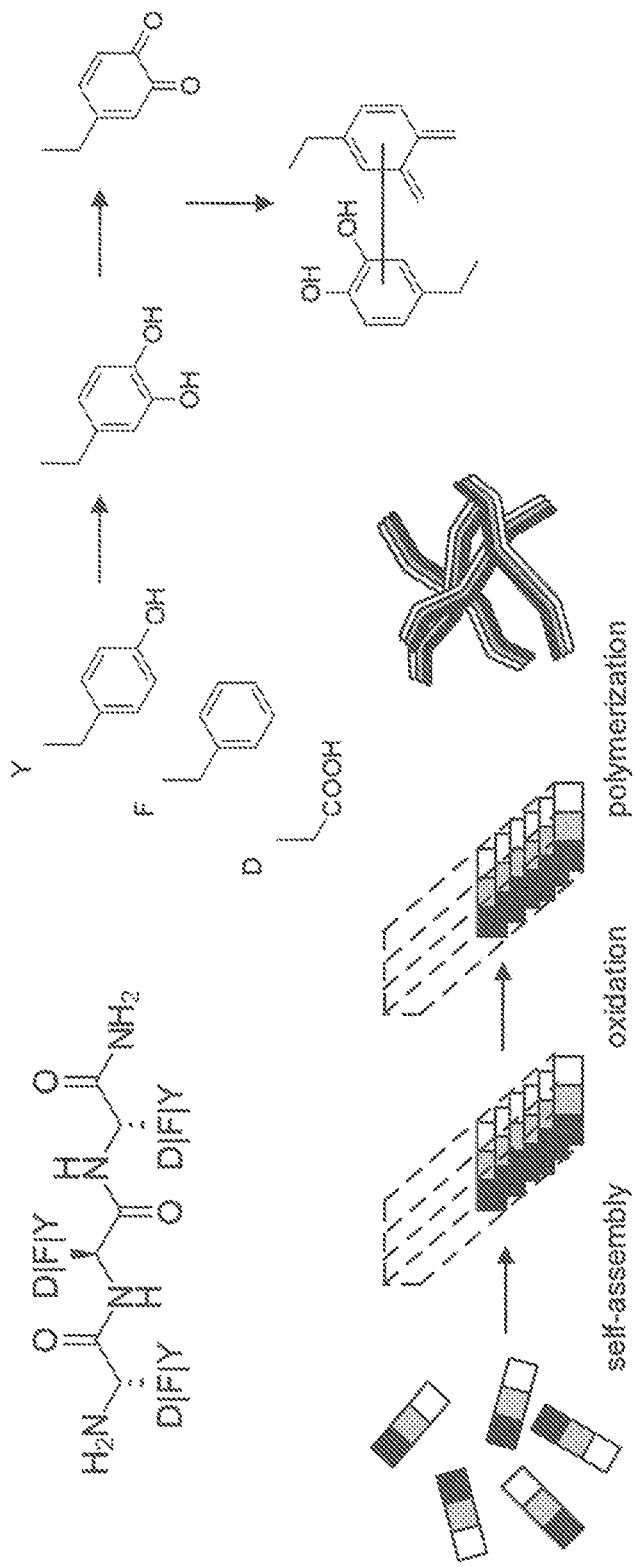
FIG. 1A is a schematic representation of selected tripeptide sequences and the controlled formation of polymeric peptide pigments.

A small subset of peptides that self-assemble into supramolecular nanostructures with sequence-dependent properties was identified. Tripeptides containing tyrosine (Y) combined with the aggregation-prone aromatic amino acid phenylalanine (F) and a charged amino acid, aspartic acid (D) were a focal point (FIG. 1A). To increase self-assembly propensity at neutral pH conditions, C-terminal amides were used. All six possible tripeptide combinations were studied, with those that contain paired aromatics were found to favor assembly. Following annealing by temporary heating (to 75° C.) and subsequent cooling to room temperature (e.g. to about 25° C. or less than 30° C.), the six peptides exhibited distinctive macroscopic appearances (FIG. 1B, upper row, 20 mM in phosphate buffer at pH 8). For KYF the polymeric pigment may be dissolved in water and adjusted to a pH of about 7.5 (i.e. 7.2 to 7.8) instead of utilizing an annealing process. Those peptides with paired aromatics give rise to self-assembly, while FDY and YDF remained a clear solution. FYD forms a suspension composed of amorphous aggregates, YFD forms an opaque gel, DFY forms a translucent gel, while DYF forms macroscopically observed needle-like crystalline fibers, eventually giving rise to a self-supporting gel.

Figure 1B:
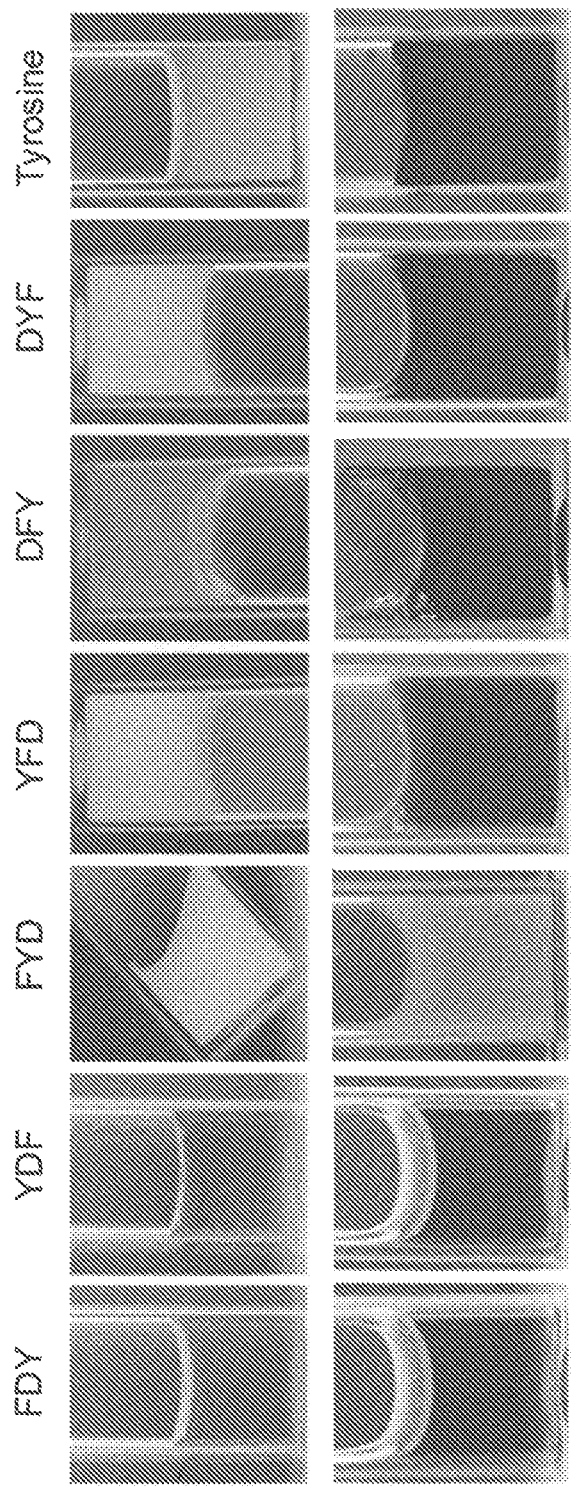
FIG. 1B are macroscopic images of the materials formed by the self-assembly of the tripeptides before (upper row) and after (lower row) 24 h of enzymatic oxidation (0.2 µg/µL) including oxidation of a tyrosine as a control.

The variable peptide assemblies were leveraged to control formation of polymeric pigments initiated by enzypatic oxidation of tyrosine residues. Tyrosinase from *Agaricus bisporus* was used, which typically oxidizes tyrosine into 3,4-dihydroxyphenylalanine (DOPA) and further oxidation products, including DOPA-quinone, DOPAchrome and dihydroxyindole eventually forming polymers from these reactive species. Tyrosinase, which was previously shown to act upon self-assembled peptides was added directly to the tripeptide assemblies (post annealing). A readily observable, variable color change emerged for all tripeptides following 4 h incubation with colors intensifying further over 24 h, resulting in light brown coloration of transparent solutions of FDY and YDF, beige coloration for the milky FYD suspension to brown-black colors for YFD, DFY and DYF, suggesting that the oxidized peptides polymerized to different extents (FIG. 1B, lower row). As a control, tyrosine was used which rapidly oxidized and polymerized, as observed by the black color of the sample and the polymeric precipitate.

Figure 2A:
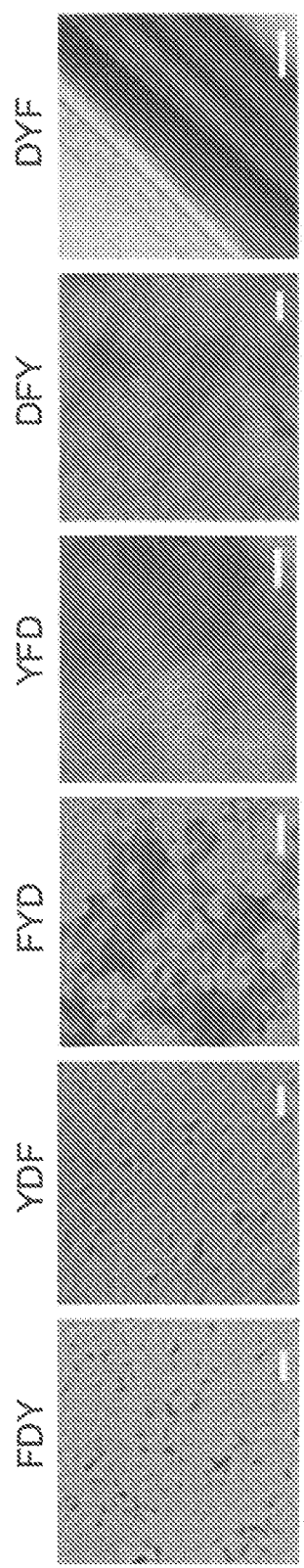
FIG. 2A are TEM micrographs of the structures formed by self-assembly of the tripeptides.

Nanoscale morphologies were determined by transmission electron microscopy (TEM) (FIG. 2A, Scale bars are 100 nm) and AFM showing that nanostructures' stiffness depends on peptide sequence. YFD and DFY assemble into a dense network of nanofibrils, while needle-like crystalline fibers are seen in DYF with amorphous aggregates observed for the others. In order to assess supramolecular order, the crystallization of DYF provides a convenient starting point. Single crystal X-ray diffraction (XRD) revealed five main interfaces that stabilize the crystal lattice. Along the x-axis, the peptides form parallel β-sheets that extend laterally by two interfaces along the y direction: hydrogen bonding between the amide groups (upper left corner) and salt bridges of the aspartate carboxylate groups and terminal amines (lower left corner). Along the z-axis, the β-sheets are packed through hydrogen bonding of the tyrosine hydroxyl groups (upper right corner) and aromatic stacking (lower left corner) into a 3D lattice. Single crystals could also be obtained by slow cooling of YFD solution. XRD shows similar interactions to DYF but with different consequences: for YFD a single backbone-backbone hydrogen bond was observed between molecules. The columns interact laterally by aromatic stacking (upper left), yielding two-dimensional planes of aromatically stacked groups, and by alternating hydrogen bonding networks coupling the aspartate/amine salt bridges (upper right), C-terminal amides and tyrosine hydroxyl groups through well-ordered water molecules (lower right). The consequence of the observed packing is a substantially different orientation of the paired aromatics—in opposite (anti) or same (syn) orientations for DYF and YFD with respect to the peptide backbone.

Figure 2B:
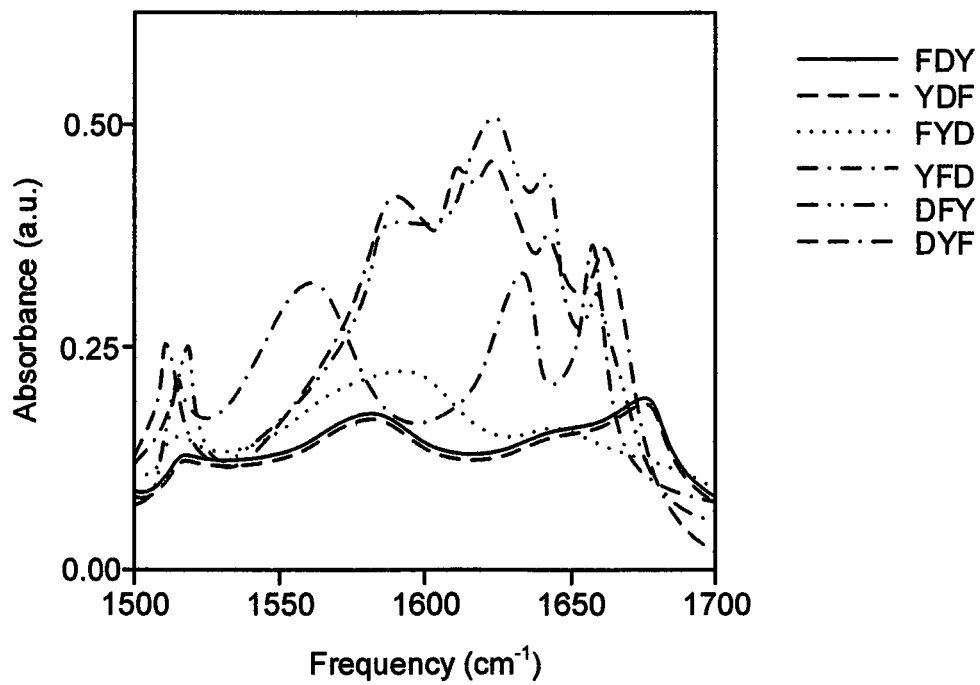
FIG. 2B is an FTIR absorption spectra of the tripeptides.

To shed more light on the organization of the tripeptides, including those for which crystal structures could not be obtained under the assembly conditions, Fourier transform infrared spectroscopy (FTIR) was used (FIG. 2B, 20 mM in $D_2O$ phosphate buffer at pH 8). FDY, YDF and FYD did not show evidence of periodically organized intermolecular interactions, as indicated by broad bands at 1,652 $cm^{-1}$ (internal amide) and 1,672 $cm^{-1}$ (terminal amide) in the FTIR spectrum, which is in agreement with observed disorder by TEM. For the assembled DFY and DYF peptides, these bands redshift to 1,620-1,640 $cm^{-1}$ and 1,658 $cm^{-1}$ respectively, which suggests a β-sheet-like organization. The YFD spectrum implies a different packing geometry, with additional narrow, redshifted bands in the amide region, but an additional shift of the aspartate carboxylate band from 1,580 $cm^{-1}$ to 1,560 $cm^{-1}$, implying intramolecular salt bridge formation with the amine group of the N-terminus in agreement with the crystal structure, which helps to stabilize paired aromatics in the syn configuration.

The six peptides show variable crystallinity. FYD, YFD, and DYF form highly crystalline materials and DFY shows lower crystallinity, evidenced by the peak intensity and broadness. In contrast, FDY and YDF are amorphous materials. However, all the peptides share some common features in terms of molecular stacking, reflecting by the peaks at the ranges of 4.4-4.8 Å and 2.9-3.2 Å. In addition, the diffraction patterns of DFY and DYF are similar, indicating the structural resemblance of these two peptides.

Figure 2C:
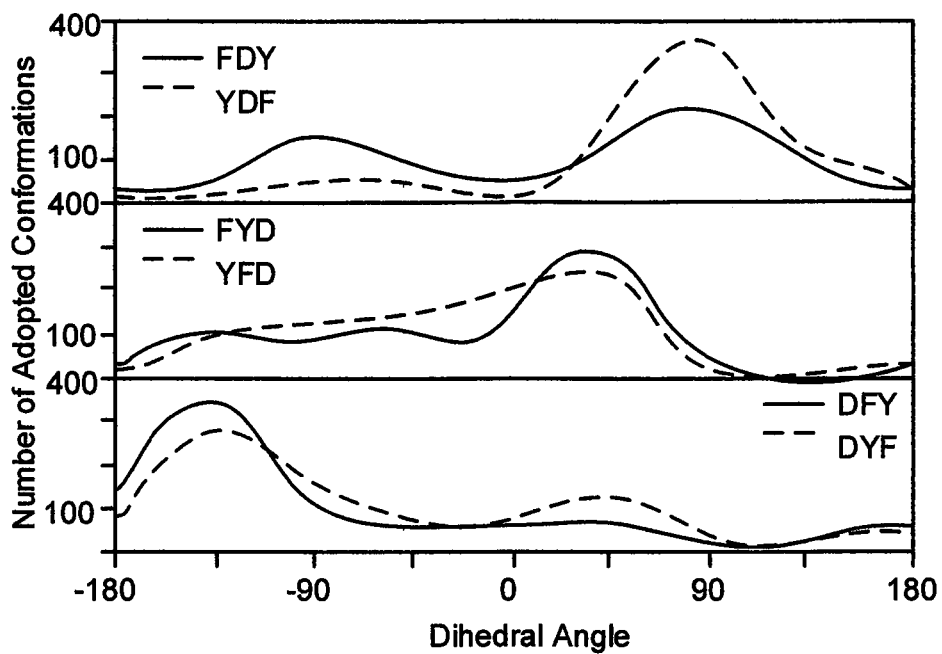
FIG. 2C shows the distribution of the CZ(Tyr)-CA(Tyr)-CA(Phe)-CZ(Phe) dihedral angle.
Figure 2D:
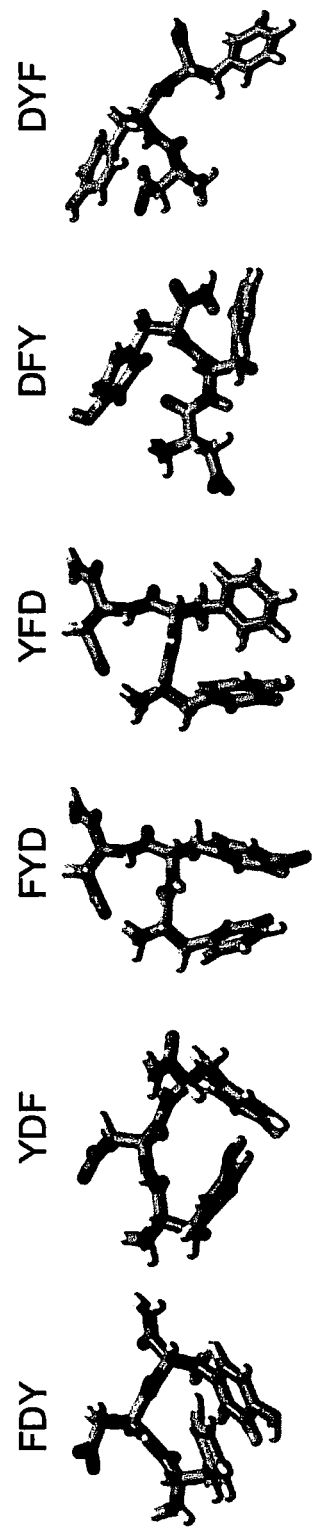
FIG. 2D depicts the preferred conformations for each peptide.

In order to examine the relative stability of the different conformations of the monomers, MD simulations were carried out (FIG. 2C, FIG. 2D). FIG. 2C depicts the distribution of the CZ(Tyr)-CA(Tyr)-CA(Phe)-CZ(Phe) dihedral angle for each peptide over the course of 50 ns indicating the greatest populated angle. The results demonstrate that the six peptides have different preferential conformations which is reflected both in the assembled state and in solution, depending on a pair-wise manner on the positions of the aspartic acid. The following relationships exist: tyrosine and phenylalanine residues are presented in anti configuration, (DXX), or syn (XXD) which is in agreement with the crystal structures obtained. When the aspartic acid is in the central position (XDX) the preferred conformations have dihedral angles of about 90°, which limits the potential for extended stacking.

Figure 3A:
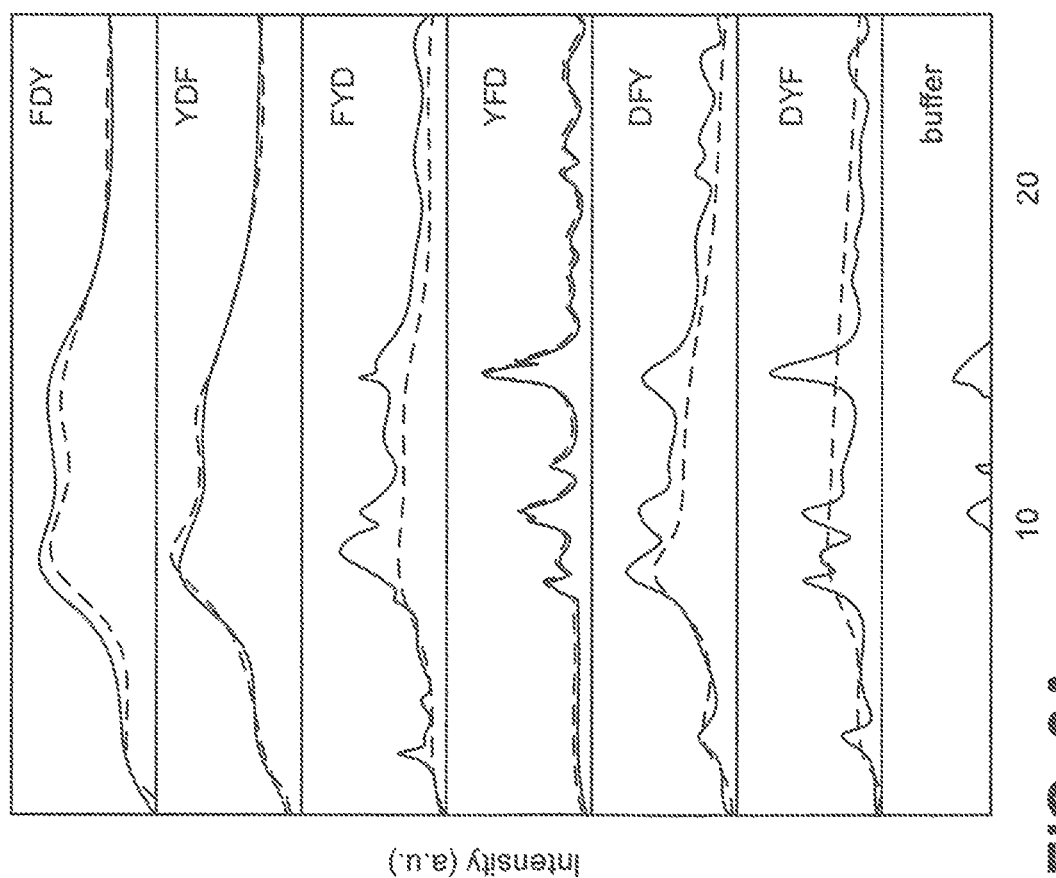
FIG. 3A is WAXS analysis in 1D of the tripeptides before (solid lines) or after (dashed lines) enzymatic oxidation.
Figure 3B:
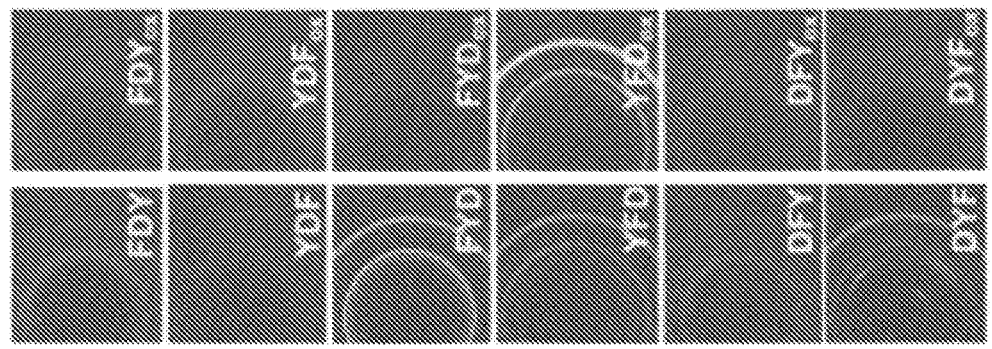
FIG. 3B is a WAXS analysis in 2D.
Figure 3C:
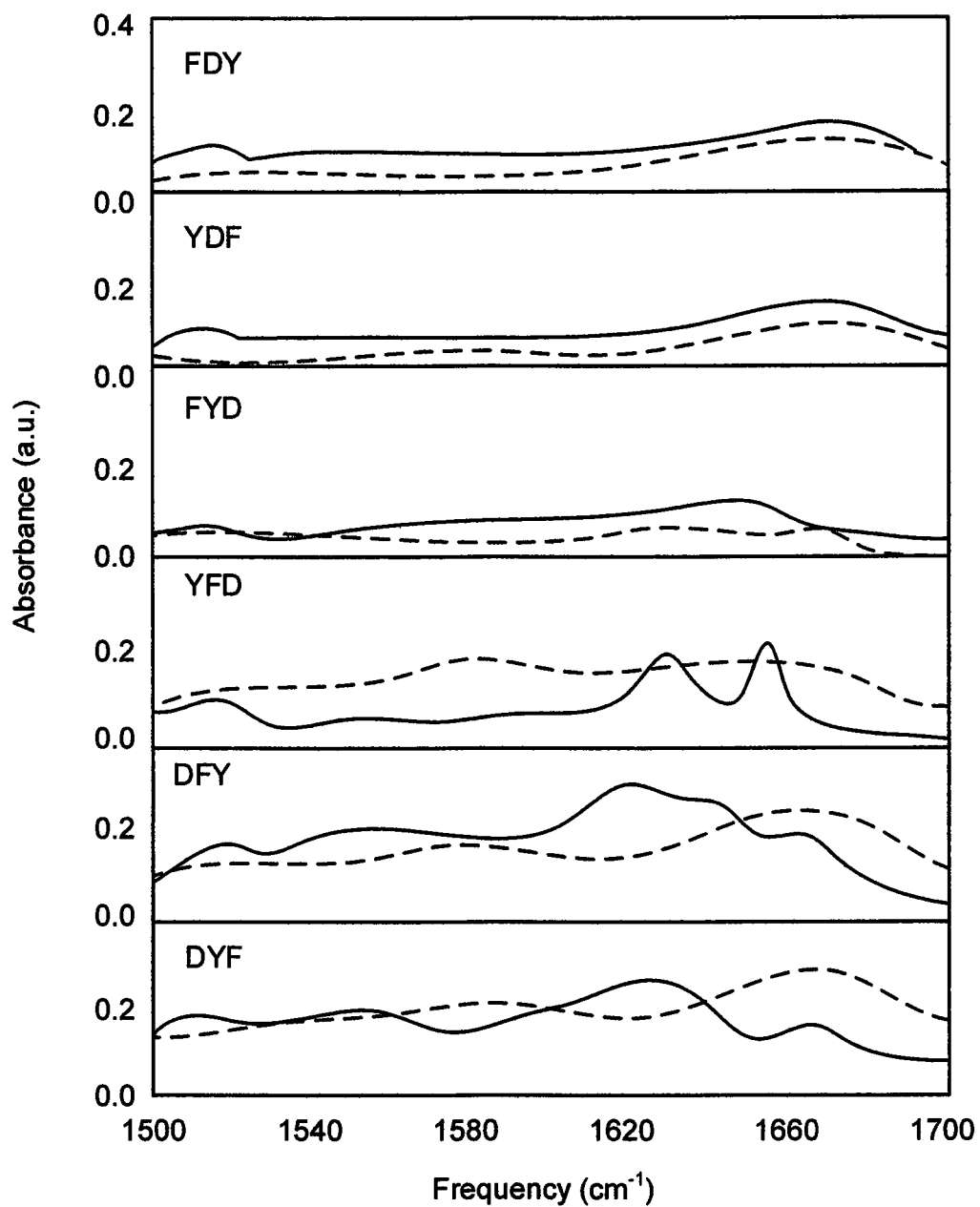
FIG. 3C is an FTIR absorption spectra of tripeptides before (solid lines) and after (dashed lines) enzymatic oxidation.

There is the possibility that the pair-wise sequence-dependent supramolecular order of the peptides influences enzymatic oxidation and further polymerization pathways. WAXS and solid phase FTIR data show loss of order with the strongest effect observed for oxidized DXX ($DXX_{ox}$), less in $XXD_{ox}$, while $XDX_{ox}$ remain disordered (FIG. 3A showing 1D, FIG. 3B showing 2D, FIG. 3C). FIG. 3B shows before (left column) and after (right column) 24 h of enzymatic oxidation. The peptides showed loss of supramolecular order (FIG. 3A, FIG. 3B) while retaining few structural features corresponding to the molecular packing, according to the peaks at about 4.5 and 2.9 Å. The FTIR spectra (FIG. 3C) show narrow, redshifted absorptions of the amide group in FYD, YFD, DFY and DYF that disappear upon oxidation in favour of broad absorptions at 1,650-1,675 $cm^{-1}$. Additionally, tyrosine-specific ring modes are lost (e.g. 1,516 $cm^{-1}$) and a new band absorption assigned to quinone is observed around 1,680 $cm^{-1}$, confirming catechol oxidation.

HPLC analysis showed (near-)complete conversions of peptides to oxidation products for both the disordered ($XDX_{ox}$) and highly ordered ($DXX_{ox}$) peptides with lower conversions observed for disordered $XXD_{ox}$ (disordered FYD to a lesser extent compared to YFD. Under the conditions examined, peptide assembly has a more pronounced effect on oxidation and polymerization compared to the position of the tyrosine within the tripeptides. Early stage conversions are higher for $XDX_{ox}$ peptides compared to the assembling counterparts. However, early stage kinetics are similar for the non-assembling $FDY_{ox}$ and $YDF_{ox}$. The overall polymerization process is believed to be dictated by supramolecular order of the precursors and less by enzyme affinity.

Figure 3D:
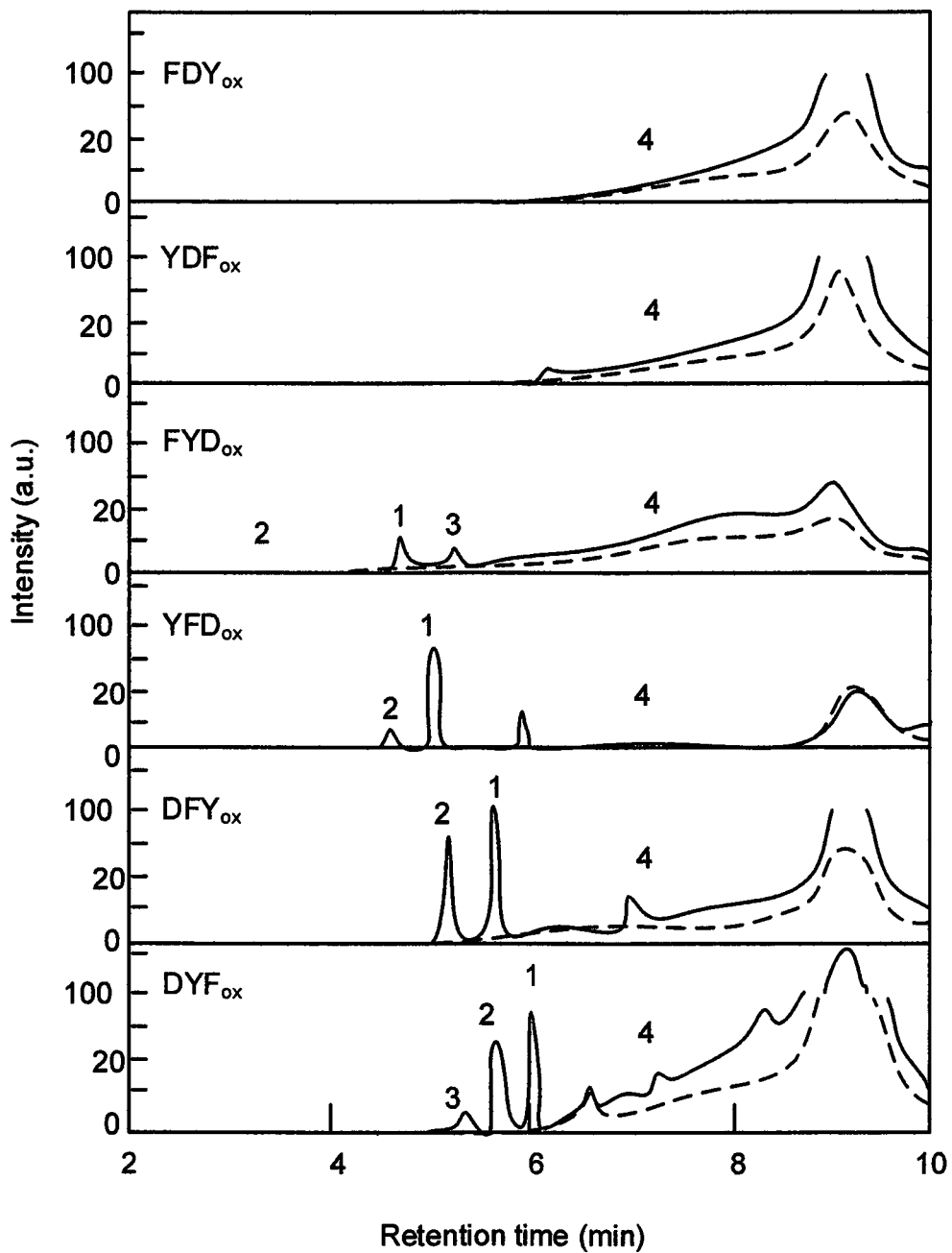
FIG. 3D depicts LC-MS chromatograms at 280 nm (solid lines) and 350 nm (dashed lines) of the soluble fraction of oxidized tripeptides.
Figure 3E:
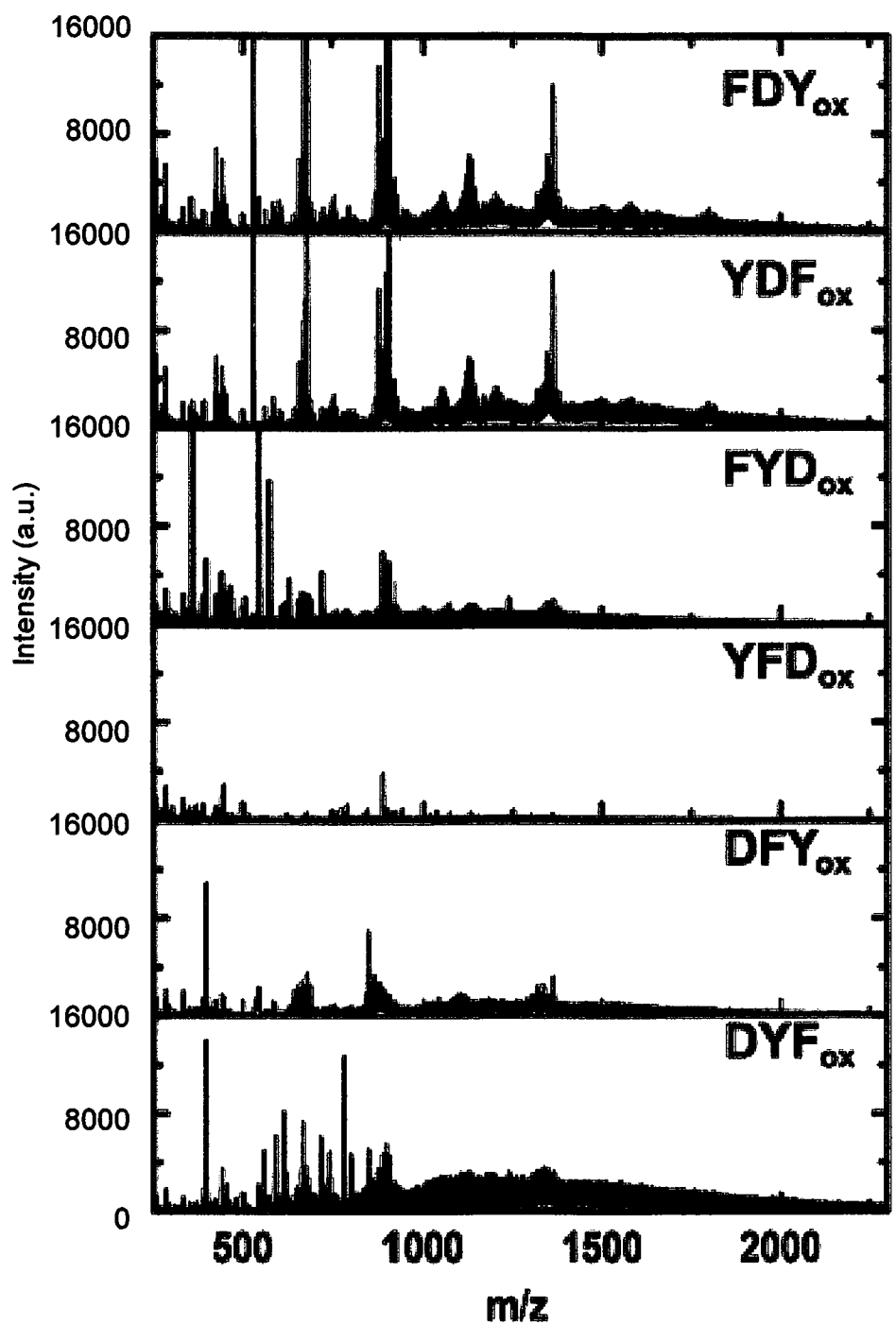
FIG. 3E is a spectra summing m/z intensities of soluble higher molecular weight polymers composed of heterogeneously connected monomers.
Figure 3F:
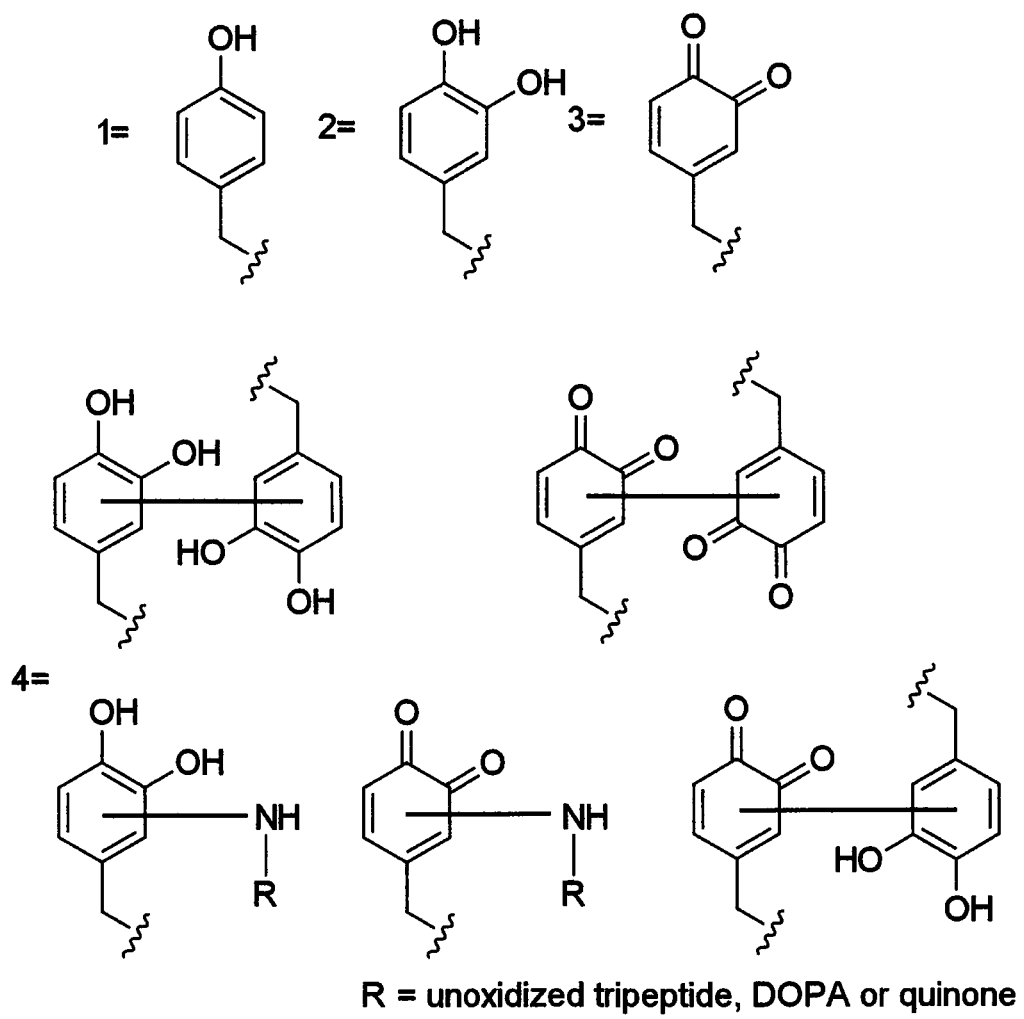
FIG. 3F depicts chemical structures of the non-oxidized peptides and their oxidation products.

LCMS data obtained after 24 h of oxidation reveal the expected catechol and quinone, as well as a wide range of dimieric and trimeric species with different connections (FIG. 3D; FIG. 3E). FIG. 3D shows LC-MS chromatograms 280 nm (solid) and 350 nm (dashed) of soluble fraction 24 h oxidized tripeptides. FIG. 3E shows the summed m/z intensities of soluble higher molecular weight polymers composed of heterogeneously connected monomers (F4) elute between 8-10 minutes. It is clear from these data that there is again a pair-wise relationship, with $XDX_{ox}$ peptides giving rise to complete conversion of the precursors to oligomers and polymers, $XXD_{ox}$ giving medium conversion with intermediate polymerization and both $DXX_{ox}$ peptides giving rise to formation of extensive oligomeric and polymeric species (FIG. 3D). In each case, the UV absorbance of polymeric species is significantly red-shifted from precursors, as would be expected for an extensive catechol/quinone network. FIG. 3F depicts chemical structures of the non-oxidized peptides (1) and the oxidation products 3,4-dihydroxyphenylalanine (2) and 3,4-quinone (3) in the context of tripeptides. (4) Connectivity of potential aryl cross-linked and Michael addition products.

Figure 4A:
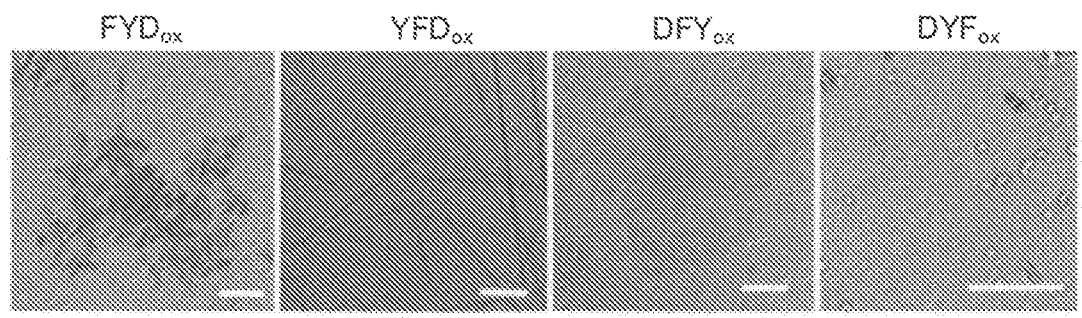
FIG. 4A are optical microscopic images of structures formed by the polymeric peptide pigments at the micron scale.

The polymers have distinct morphologies as seen by optical microscopy (FIG. 4A). While oxidized YFD ($YFD_{ox}$) maintains a one-dimensional morphology, it forms much larger fibers, suggesting a degree of lateral aggregation which may be facilitated by the positioning of 2D sheets of reactive aromatic species at interfaces, as seen in the crystal structure. $DFY_{ox}$ polymerizes into extended 2D sheets while $DYF_{ox}$ forms spheres. These morphologies, and the amorphous structures of the other oxidized peptides, were also observed by TEM. While the $DFY_{ox}$ sheets and $YFD_{ox}$ fibers are found in the solid phase, the $DYF_{ox}$ spheres remain dispersed in the aqueous buffer.

The most contrasting structures formed are evident in $DXX_{ox}$ tripeptides showing high levels of polymerization accompanied with loss of order starting from similar molecular packing of the precursors. For these peptides, a subtle difference in sequence dictates the initial (crystalline fibers vs supramolecular fibers) and oxidized (spheres vs sheets) morphology. For $DFY_{ox}$, it is believed that the anti conformation of aromatic side chains is favorable for polymerization along the length of the β-sheet, but also laterally between neighboring fibrils, eventually resulting in loss of supramolecular structures (fibrils) and formation of extended, micron-scale 2D sheets. Time course TEM analysis of DFY supports this mechanism for the fiber-to-sheet transition, revealing the formation of dark layers on the fibrils' surface (4 h); these layers further assemble and polymerize into 2D sheets that extend from the fiber surface (1 week). For DYF, a different orientation of tyrosine gives rise to an additional stabilizing interaction (Tyr-Tyr) within the DYF crystal lattice. Oxidation of tyrosine eliminates H-bonding in these residues thereby disrupting the crystalline fiber and reconfiguring the peptides into spherical assemblies. These data are in agreement with the loss of the original packing and subsequent polymerization observed for both $DFY_{ox}$ and $DYF_{ox}$ by FTIR, WAXS and LCMS (FIG. 3A-D).

Figure 4B:
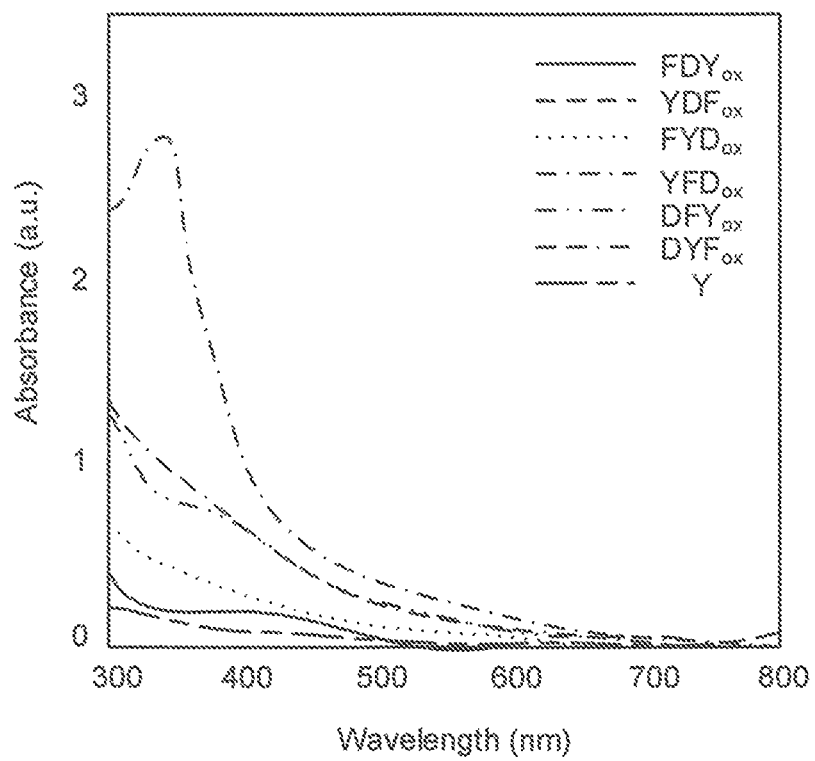
FIG. 4B is a UV-Vis absorption spectra of solution fractions of the polymeric peptide pigments or oxidized tyrosine.

The results show that supramolecular order in peptide precursors can be systematically converted into disordered polymeric pigments, resulting in variable characteristics that relate to their functionality (FIG. 4A). FIG. 4A depicts structures formed by the polymeric peptide pigments at the micron scale using optical microscopy. Scale bars for $FYD_{ox}$, $YFD_{ox}$ and $DFY_{ox}$ are 20 μm and 10 μm for $DYF_{ox}$. UV-Vis measurements showed different broadband spectra with $DFY_{ox}$ showing absorption throughout the visible region (420-650 nm) and the high absorption observed for $FYD_{ox}$ possibly contributed by highly scattering aggregates (FIG. 4B). The observed maximum around 340 nm for $YFD_{ox}$, together with the LCMS (FIGS. 3D-E) and HPLC analyses suggest that the N-terminal positioning of the catechol results in a lower degree of connectivity and cross-linking.

Figure 4C:
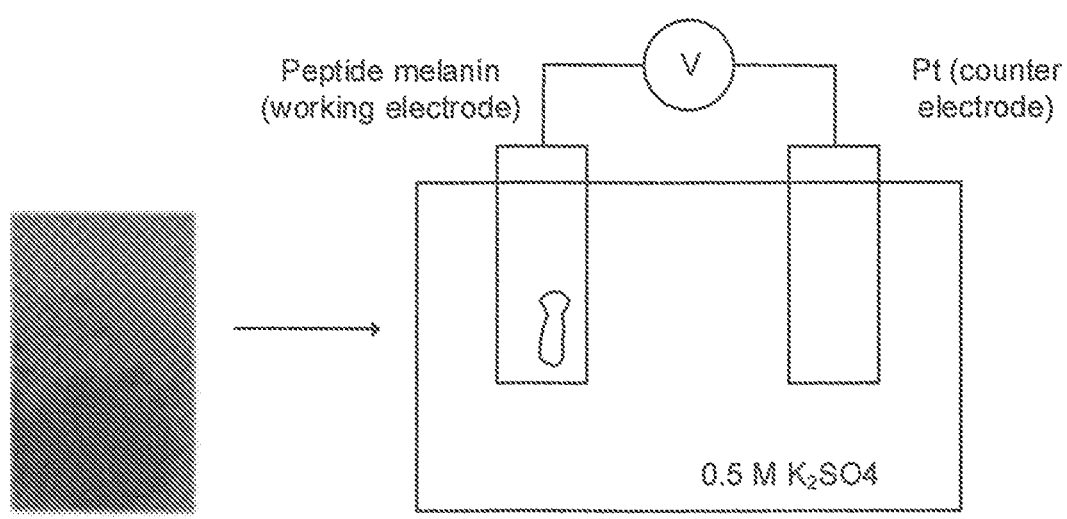
FIG. 4C is a schematic depiction of the electrochemical cell used for discharge measurements.
Figure 4D:
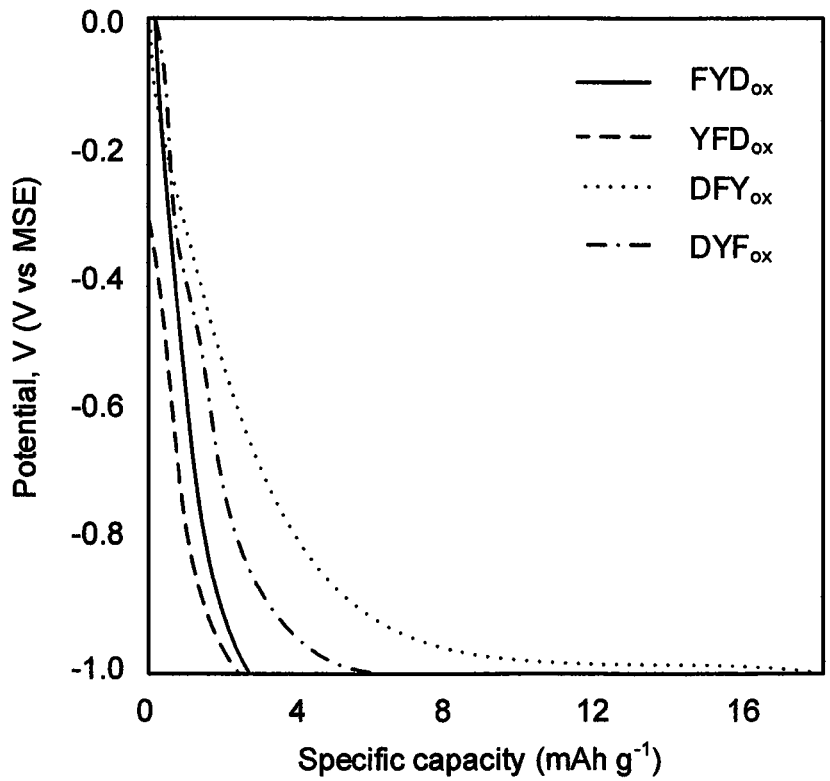
FIG. 4D is a graph depicting electrochemical potential profiles.
Figure 4E:
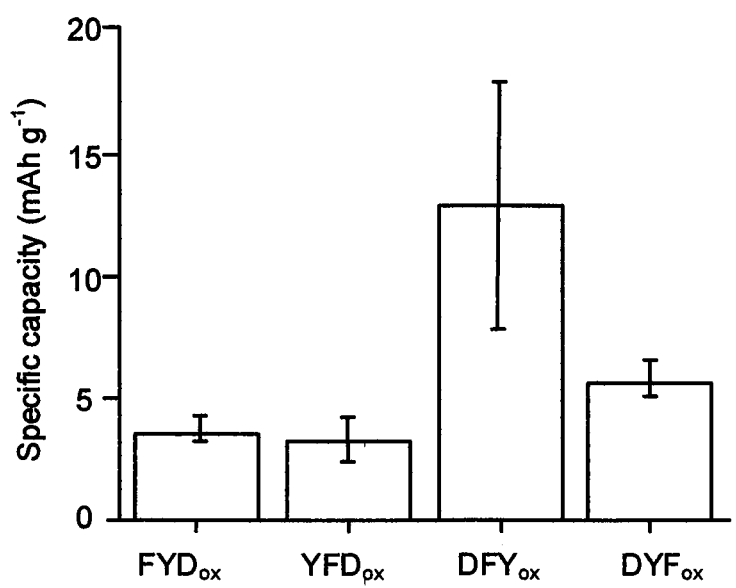
FIG. 4E is a graph of average specific capacity of polymeric peptide pigments or oxidized tyrosine.

Oxidized peptides were configured into cathodes in aqueous half-cell configurations. The charge storage capacity can provide an estimate of the concentration of redox-active components while the shape of the discharge curve can provide insight into the distribution of morphological phases. For this purpose, electrodes were fabricated by compacting peptide melanin powders into a stainless steel support mesh (FIG. 4C). For all systems tested, the potentials become monotonically more negative during discharge, which confirms that these materials are largely disordered. $DFY_{ox}$ 2D sheets exhibit the highest specific charge storage capacity, followed by $DYF_{ox}$ (FIG. 4D; FIG. 4E) which is attributed to an increase in the concentration of redox active tyrosine-based derivatives, and is confirmed by cyclic voltammetry CV. FIG. 4E shows average specific capacity of polymeric peptide pigments or oxidized tyrosine (N=3). Capacitive storage is the likely source of differential capacities in cathodes composed of $YFD_{ox}$ versus $FYD_{ox}$, which are otherwise largely devoid of redox behavior as assessed by CV. The specific capacity of $DFY_{ox}$ is comparable to that measured in natural eumelanin cathodes and less than that of the synthetic melanin-based cathodes. CV of $DFY_{ox}$-based cathodes showed multiple redox peaks that are not commonly observed in other types of natural and synthetic melanin-based pigments, attributed to presence of multiple types of polyphenols, with a variety of redox behavior. Electron paramagnetic resonance (EPR) suggests that $DFY_{ox}$ sheets exhibit the highest gravimetric concentration of radical content among the polymeric peptide pigments. It is believed that relatively higher semiquinone concentrations correspond to not only higher overall concentrations of catechols, but also molecular configurations that permit comproportionation reactions. The attenuated EPR signal observed in the polymeric peptide pigments is consistent with this model owing to the smaller overall catechol concentrations and reduced catechol-catechol interactions compared to natural eumelanins.

To expand the sequence variety of polymeric peptide pigments' substrates, the tripeptide KYF was selected, containing the amino acids lysine (K), tyrosine (Y), and phenylalanine (F) and examined the polymeric material formed by oxidizing the pre-assembled peptide nanostructures.

The peptide forms a translucent soft gel containing nanofibrils at 20 mM in distilled water at pH 7.5. A color change emerged following 4 h of oxidation with tyrosinase (0.2 μg/μl) with a reddish-brown color intensifying further over 24 h (FIG. 5A). The polymeric material formed by oxidized KYF ($KYF_{ox}$) has distinctive spherical morphology as seen by optical microscopy (FIG. 5B). Transmission electron microscopy (TEM) revealed formation of small spherical structures following 4 h of oxidation, alongside pre-oxidized fibrils and larger spheres with a diameter of 700 $nm^{-1}$ μm form following 24 h of oxidation (FIG. 5C). Scanning electron microscopy (SEM) showed the deposition of $KYF_{ox}$ polymeric spheres with a diameter of 200 nm-700 nm (FIG. 5D).

Figure 6A:
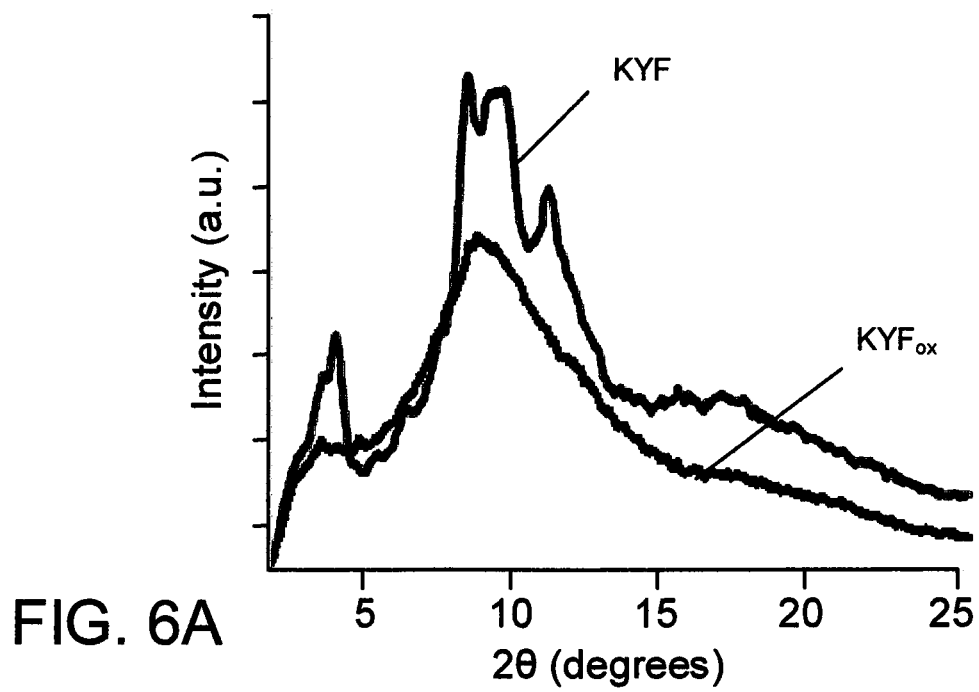
FIG. 6A is a WAXS analysis of KYF before (solid line) or after (dashed line) 24 h of enzymatic oxidation.
Figure 6B:
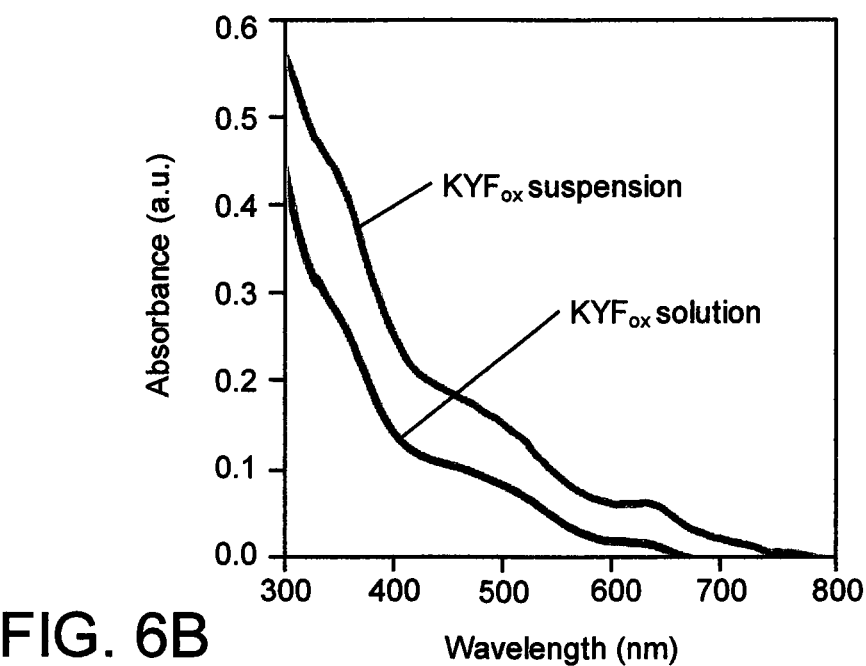
FIG. 6B is a UV-Vis absorption spectra of solution (solid line) and suspension (dashed line) fractions of $KYF_{ox}$ polymeric pigment.

Wide angle x-ray scattering (WAXS) analysis of KYF showed loss of supramolecular order following oxidation (FIG. 6A). UV-Vis measurements of $KYF_{ox}$ polymeric pigment following centrifugation (10 min at 15,000 g) showed broadband spectra with maxima at 360 nm, 500 nm, and 630 nm (FIG. 6B).

This disclosure demonstrates the ability to leverage differential assembly and reactivity to achieve tunable polymeric pigments, and find that supramolecular order in precursors is inversely correlated to disorder in resulting polymers. This gives rise to control and tunability over the properties of the materials.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of forming a polymeric peptide pigment, the method comprising sequential steps of:
    forming an aqueous, phosphate-buffered solution of a peptide, the peptide being selected from a group consisting of DFY-NH$_2$, FYD-NH$_2$, YFD-NH$_2$, and DYF-NH$_2$, wherein the peptide is present in the aqueous, phosphate-buffered solution at a concentration of at least 20 mM;

annealing the aqueous, phosphate-buffered solution by heating the aqueous, phosphate-buffered solution to 75° C. and subsequently cooling the aqueous, phosphate buffered solution to about 25° C., wherein the peptides self-assemble to form a supramolecular structure;

enzymatically oxidizing the peptide to initiate a polymerization reaction using a tyrosinase enzyme, the polymerization reaction forming a polymeric peptide pigment.

2. The method as recited in claim 1, wherein the peptide is DFY-NH$_2$ and the supramolecular structure is a translucent gel.

3. The method as recited in claim 1, wherein the peptide is YFD-NH$_2$ and the supramolecular structure is an opaque gel.

4. The method as recited in claim 1, wherein the peptide is FYD-NH$_2$ and the supramolecular structure is an amorphous aggregate.

5. The method as recited in claim 1, wherein the peptide is DYF-NH$_2$ and the supramolecular structure is a crystalline fiber.

* * * * *